United States Patent
Auguste et al.

(10) Patent No.: US 9,795,624 B2
(45) Date of Patent: Oct. 24, 2017

(54) CATIONIC POLYMERS AS CO-DRUGS FOR CHEMOTHERAPEUTIC AGENTS

(71) Applicant: Research Foundation of the City University of New York, New York, NY (US)

(72) Inventors: Debra Auguste, Briarcliff Manor, NY (US); Daxing Liu, New York, NY (US)

(73) Assignee: RESEARCH FOUNDATION OF THE CITY UNIVERSITY OF NEW YORK, New York, NY (US)

(*) Notice: Subject to any disclaimer, the term of this patent is extended or adjusted under 35 U.S.C. 154(b) by 0 days.

(21) Appl. No.: 15/146,451

(22) Filed: May 4, 2016

(65) Prior Publication Data

US 2016/0324883 A1 Nov. 10, 2016

Related U.S. Application Data

(60) Provisional application No. 62/156,509, filed on May 4, 2015.

(51) Int. Cl.

| | | |
|---|---|---|
| A61K 31/785 | (2006.01) |
| A61K 47/34 | (2017.01) |
| A61K 31/704 | (2006.01) |
| A61K 38/17 | (2006.01) |
| A61K 45/06 | (2006.01) |
| A61K 31/506 | (2006.01) |
| A61K 31/513 | (2006.01) |
| A61K 31/7068 | (2006.01) |

(52) U.S. Cl.
CPC .......... *A61K 31/704* (2013.01); *A61K 31/506* (2013.01); *A61K 31/513* (2013.01); *A61K 31/7068* (2013.01); *A61K 31/785* (2013.01); *A61K 38/1706* (2013.01); *A61K 45/06* (2013.01); *A61K 47/34* (2013.01)

(58) Field of Classification Search
CPC .. A61K 31/337; A61K 31/704; A61K 31/785; A61K 47/34
See application file for complete search history.

(56) References Cited

U.S. PATENT DOCUMENTS

| | | | |
|---|---|---|---|
| 8,835,172 B2 | 9/2014 | Delehanty et al. | |
| 2006/0041058 A1* | 2/2006 | Yin .................. | A61K 47/48961 525/50 |
| 2006/0078535 A1* | 4/2006 | Livant .............. | A61K 47/48961 424/78.27 |
| 2010/0331273 A1* | 12/2010 | Medina-Kauwe | A61K 47/48246 514/34 |
| 2014/0142166 A1* | 5/2014 | Ventura ............... | A61L 27/18 514/449 |
| 2014/0336571 A1* | 11/2014 | Slager ................. | A61K 31/337 604/95.03 |
| 2016/0312218 A1* | 10/2016 | Zhu .................. | A61K 47/48907 |

FOREIGN PATENT DOCUMENTS

WO   WO03106491   12/2003

OTHER PUBLICATIONS

Deepthi, A. et al.; Targeted Drug Delivery to the Nucleus and its Potential Role in Cancer Chemotherapy; J. Pharm. Sci. & Res.; 2013; pp. 48-56; vol. 5, Issue 2; JPSR.

Dong, D. et al.; Comparative studies of polyethylenimine-doxorubicin conjugates with pH-sensitive and pH-insensitive linkers; Journal of Biomedical Materials Research A; Oct. 15, 2012; pp. 1336-1344; vol. 101A, Issue 5; Wiley Periodicals, Inc.

Jung, H. et al; Linear Polyethyleneimine-Doxorubicin Conjugate for pH-Responsive Synchronous Delivery of Drug and MicroRNA-34a; Macromolecular Research; 2015; pp. 449-456; vol. 23, No. 5; The Polymer Society of Korea and Springer.

Cheng, W.; et al.; Novel amphiphilic polyethylenimine (PEIs) for oral delivery of poorly soluble drugs; Journal of Pharmacy and Pharmacology; Sep. 2004; pp. s34-s35; vol. 56, Issue 1.

* cited by examiner

*Primary Examiner* — Jeffrey E Russel
(74) *Attorney, Agent, or Firm* — Hamilton, Brook, Smith & Reynolds, P.C.

(57) ABSTRACT

A method for treating a biological cell is disclosed. The method administers a mixture of a chemotherapeutic drug and a co-drug that facilitates delivery of the chemotherapeutic drug to the nucleus of the cell. Examples of co-drugs include cationic polymers, cationic lipids and cationic proteins. Cationic polymers include a polyethyleneimine (PEI), polylysine, a polybetaaminoester (PBAE), an ε-polylysine (EPL) including ε-poly-L-lysine (e-PLL), a polyarginine peptide, chitosan, a polyamidoamine dendrimer (PAMAM). Cationic lipids include 1,2-dioleoyl-3-trimethylammonium-propane (DOTAP). Cationic proteins include protamine.

10 Claims, 16 Drawing Sheets

CATIONIC POLYMERS AS CO-DRUGS FOR CHEMOTHERAPEUTIC AGENTS

CROSS-REFERENCE TO RELATED APPLICATIONS

This application claims priority to and is a non-provisional of U.S. Patent Application Ser. No. 62/156,509 (filed May 4, 2015), the entirety of which is incorporated herein by reference.

STATEMENT OF FEDERALLY SPONSORED RESEARCH OR DEVELOPMENT

This invention was made with government support under contract no. 1DP2 CA174495-01 awarded by the National Institute of Health (NIH). The government has certain rights in the invention.

BACKGROUND OF THE INVENTION

The subject matter disclosed herein relates to the treatment of cancer. Numerous treatments of cancer are currently in use. Chemotherapeutic drugs are often used to induce cell death. Ideally, these drugs are used in low concentrations to minimize undesirable side effects that may be caused by the drugs. Unfortunately, attempts to use low concentrations often reduces the effectiveness of the drug to unacceptable levels. It would therefore be desirable to provide a new method to reduce the dosage requirements for existing chemotherapeutic drugs. The discussion above is merely provided for general background information and is not intended to be used as an aid in determining the scope of the claimed subject matter.

BRIEF DESCRIPTION OF THE INVENTION

A method for treating a biological cell is disclosed. The method administers a mixture of a chemotherapeutic drug and a co-drug that facilitates delivery of the chemotherapeutic drug to the nucleus of the cell. Examples of co-drugs include cationic polymers, cationic lipids and cationic proteins. Cationic polymers include a polyethyleneimine (PEI), polylysine, a polybetaaminoester (PBAE), an ε-polylysine (EPL) including ε-poly-L-lysine (e-PLL), a polyarginine peptide, chitosan, a polyamidoamine dendrimer (PAMAM). Cationic lipids include 1,2-dioleoyl-3-trimethylammonium-propane (DOTAP). Cationic proteins include protamine.

In a first embodiment, a method for treating a biological cell is provided. The method comprising administering a composition of matter to a biological sample, wherein the composition of matter comprises a mixture of: a chemotherapeutic drug; a co-drug selected from the group consisting of a cationic polymer, a cationic lipid, and a cationic protein wherein the chemotherapeutic drug is not covalently bound to the co-drug; and wherein the composition of matter exhibits greater cytotoxicity than either the chemotherapeutic drug or the co-drug individually.

In a second embodiment, a method for treating a biological cell is provided. The method comprising administering a composition of matter to a biological organism, wherein the composition of matter consists essentially of a mixture of: a chemotherapeutic drug; a co-drug that is a cationic polymer, wherein the chemotherapeutic drug is not covalently bound to the co-drug wherein the composition of matter exhibits greater cytotoxicity against a MDA MB-231 human breast adenocarcinoma cell line than either the chemotherapeutic drug or the co-drug individually.

In a third embodiment, a method for treating a biological cell is provided. The method comprising administering a composition of matter to a biological organism, wherein the composition of matter consists essentially of a mixture of: a chemotherapeutic drug; a linear polyethyleneimine (PEI) with a molecular weight of between 20,000 and 50,000, wherein the PEI is not covalently bound to the co-drug, wherein the composition of matter exhibits greater cytotoxicity against a MDA MB-231 human breast adenocarcinoma cell line than either the chemotherapeutic drug or the PEI individually.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Without wishing to be bound to any particular theory, it is believed that a chemotherapeutic drug should reach a cancer cell's nucleus to kill the cancer cell. Disclosed herein is a method that uses certain co-drugs to increase trafficking of a chemotherapeutic drug to the nucleus for the purpose of chemotherapeutic delivery. The disclosed method achieves nuclear delivery of the chemotherapeutic which results in enhanced toxicity at lower dosages. The method can kill cancer cells that traditional dosages of known chemotherapeutics cannot because the chemotherapeutic drug can be delivered into the nucleus.

The co-drug may be a cationic polymer like a polyethyleneimine (PEI), polylysine (linear or branched), a polybetaaminoester (PBAE) which may be linear or branched, an ϵ-polylysine (EPL) including ϵ-poly-L-lysine (e-PLL), a polyarginine peptide, chitosan, a polyamidoamine dendrimer (PAMAM) or a cationic lipid like 1,2-dioleoyl-3-trimethylammonium-propane (DOTAP), or mixtures of these co-drugs. In one embodiment, other molecules that enable nuclear delivery are included along with the co-drug.

Figure 1:
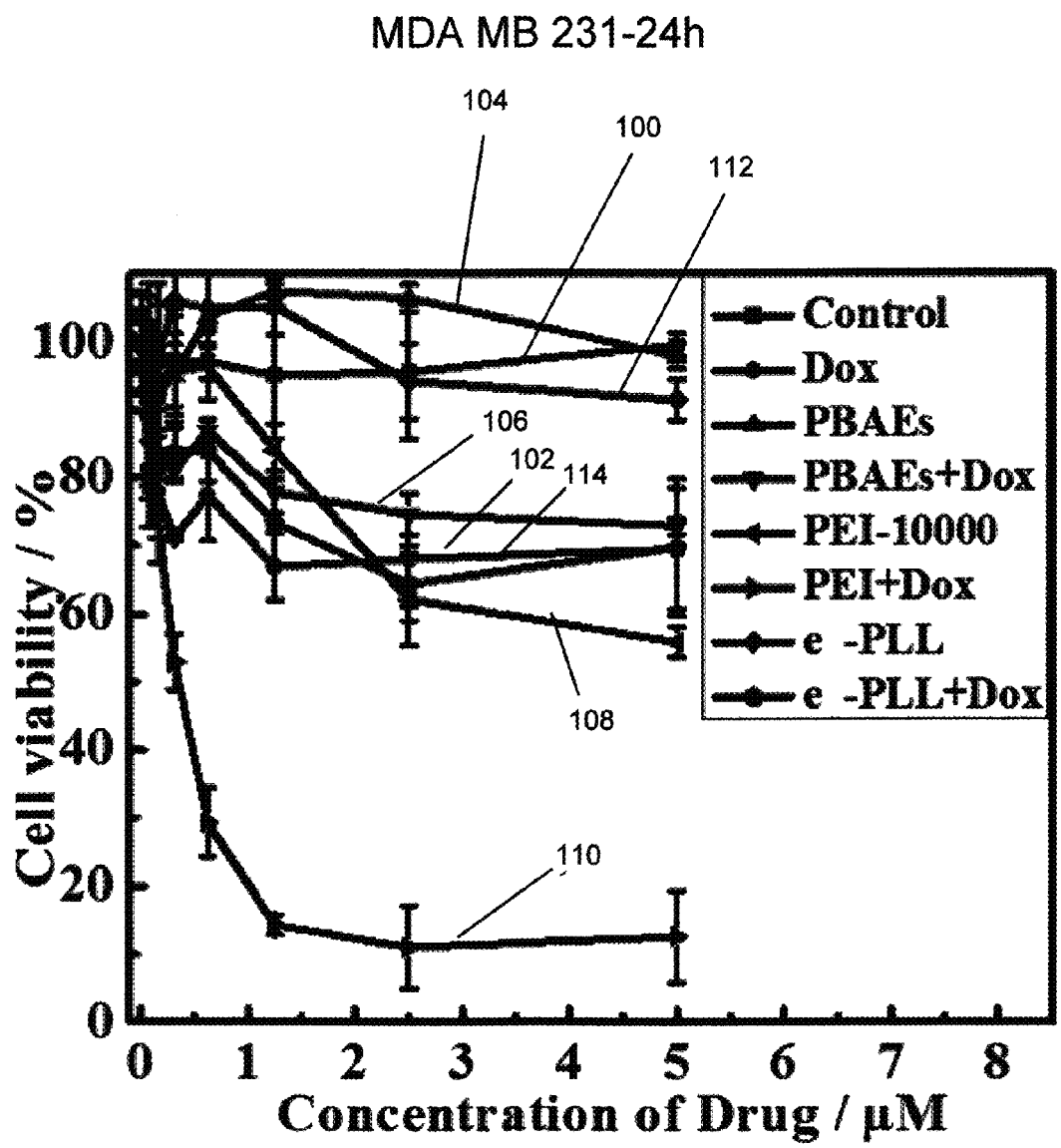
FIG. 1 is a graph depicting cell viability as a function of drug concentration for various compositions.

FIG. 1 shows the results of PEI delivered with doxorubicin. The use of the co-drug is more efficient in killing triple negative breast cancer cells, MDA-MB-231, compared to either PEI or doxorubicin alone. The disclosed method can be broadly used for a range of metastatic and chemoresistant cancers.

Line 100 shows the results of a control experiment that permitted MDA MB231 cells to grow for 24 hours. All cells were maintained at 37° C. in a humidified incubator with 5% CO2. MDA-MB-231 growing in the DMEM medium were harvested by trypsin-EDTA, and an initial concentration of 1×106 and further dilutions were made and seeded into wells of a 96-well plate (100 µL for each well). The medium without cells was used as negative control, and the plate was incubated for 18 h to allow cell attachment. Then another 100 µL medium with desirable concentration drug were added into the well. After 24 h and 48 h incubation, 22 µL of alamar-blue (0.5 mg per mL) was added to each well. The absorbance was measured after further 4 h incubation at 530 nm and 590 nm using PowerwaveXPS plate reader. The plate was also incubated for the following 24 hours to measure the maximum dye reduction. Percentage reduction of alamar-blue is typically calculated using equation (1):

$$\text{Survival Rate} == \frac{A_t - A_n \times 100\%}{A_c - A_n} \qquad (1)$$

where $A_t$, $A_n$ and $A_c$ are recorded absorbance of test wells for test group, negative control group and positive control group.

Line 102 shows the results of a doxorubicin treatment with approximately 70% cell viability, depending on drug concentration, with drug concentrations between 0 µM and 5 µM. Line 104 shows the results of a PBAE treatment at concentrations of less than 5 µM. The cell viability for PBAE was similar to that of the control line 100. Line 106 shows the results of a PBAE plus doxorubicin treatment at concentrations of less than 5 µM each. In the experiments of FIG. 1, the concentration of the polymer and doxorubicin were the equal. The graph shows approximately 75% cell viability for PBAE plus doxorubicin treatment. Line 108 shows the results of a PEI-10,000 treatment at concentrations of less than 5 µM. The graph shows approximately 60% cell viability for PEI-10,000 concentrations between 2.5 µM and 5 µM. Line 110 shows the results of a PEI-10,000 plus doxorubicin treatment at concentrations of less than 5 µM. The concentration of the polymer and doxorubicin were the equal. This particular combination showed a remarkable increase in effectiveness (cell viability of about 10%) in comparison to the results of either PEI-10,000 or doxorubicin alone. Line 112 shows the results of an e-PLL treatment at concentrations of less than 5 µM. The cell viability was similar to that of the control line 100. Line 114 shows the results of an e-PLL plus doxorubicin treatment at concentrations of less than 5 µM. The concentration of the polymer and doxorubicin were the equal. The graph shows approximately 70% cell viability for e-PLL plus doxorubicin treatment.

Figure 2:
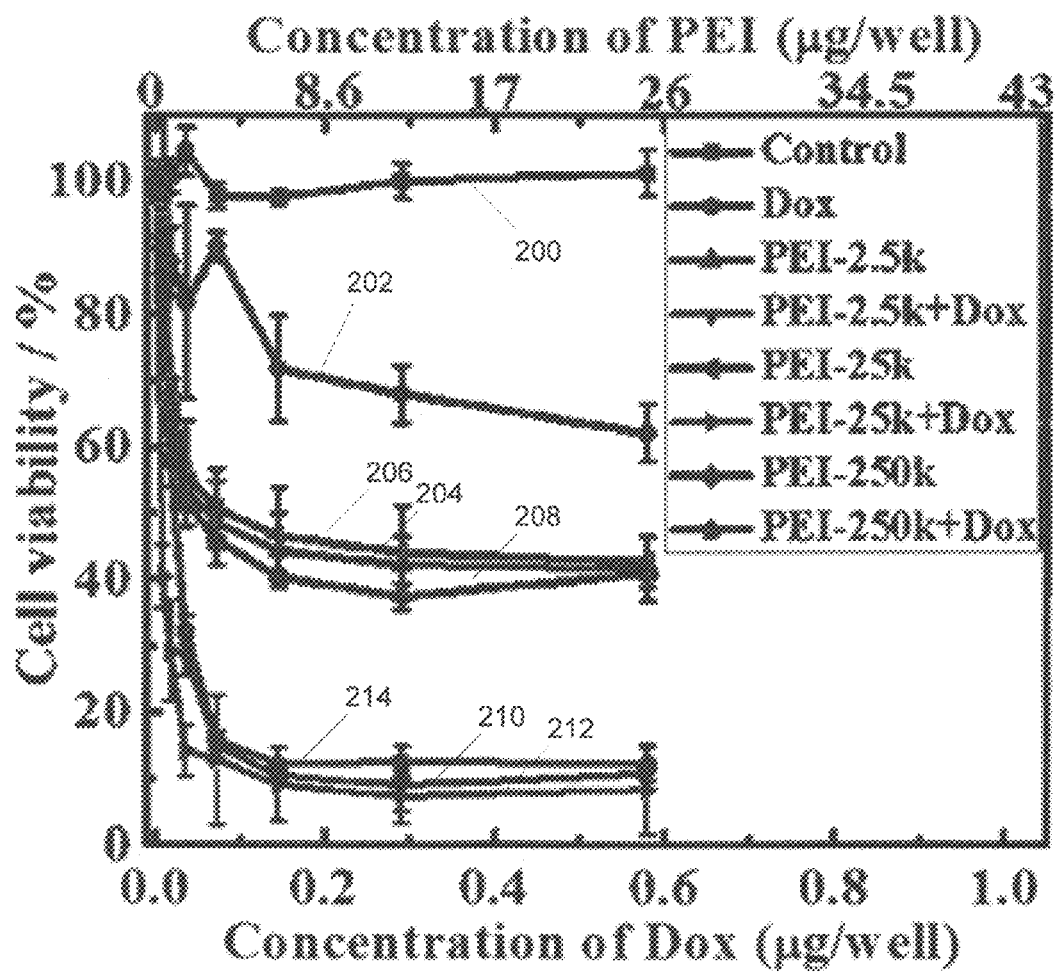
FIG. 2 is a graph depicting cell viability as a function of drug concentration and polymer composition for polymers of various molecular weights.

Referring to FIG. 2, the cell viability is shown as a function of the molecular weight of the cationic polymer. A control line 200 shows a doxorubicin-free treatment. All cells were maintained at 37° C. in a humidified incubator with 5% $CO_2$. MDA-MB-231, 4T1 and HUVECs, HCC-1806, Hs-587T, MCF-7 cells growing in the log phase of growth were harvested by trypsin-EDTA, and an initial concentration of 1×10⁶ and further dilutions were made and seeded into wells of a 96-well plate (100 µL for each well). The medium without cells was used as negative control, and the plate was incubated for 18 h to allow cell attachment. Then another 100 µL medium with desirable concentration drug were added into the well. After 24 h and 48 h incubation, 22 µL of alamar-blue (0.5 mg per mL) was added to each well. The absorbance was measured after further 4 h incubation at 530 nm and 590 nm using Powerwave XPS plate reader. The plate was also incubated for the following 24 hours to measure the maximum dye reduction. Percentage reduction of alamar-blue is typically calculated using equation (1).

Line 202 shows the results of a doxorubicin treatment with approximately 60-70% cell viability at concentrations between 0.3 and 0.6 µg doxorubicin per well and 0 µg of PEI.

Lines 204, 206, and 208 show cell viability effects of PEI alone (PEI-2.5k, PEI-25k and PEI-250k, respectively) with cell viabilities between 40-50% at PEI concentrations less than 26 µg per well.

Lines 210, 212 and 214 show cell viability effects of PEI (PEI-2.5k, PEI-25k and PEI-250k, respectively) in combination with doxorubicin with cell viabilities between 5-15% at doxorubicin concentrations of less than 0.6 µg doxorubicin per well. The ratio of the PEI to the doxorubicin was approximately 43:1 in each example.

Table 1 lists the $IC_{90}$ value of different therapies with PEI, doxorubicin and PEI and doxorubicin. In one embodiment, the PEI has a molecular weight between 10,000 and 250,000. In another embodiment, the PEI has a molecular weight between 20,000 and 100,000. In another embodiment, the PEI has a molecular weight between 20,000 and 50,000.

TABLE 1

| PEI/Dox with consistent mass of PEI | | No PEI | PEI-1.8k | PEI-10k | PEI-60k | PEI-2.5k | PEI-25k | PEI-250k |
|---|---|---|---|---|---|---|---|---|
| 24 h (mg/well) | PEI without Dox | — | — | — | — | — | — | — |
| | Dox | | — | — | — | 0.2904 | 0.1508 | 0.2904 |
| | PEI | | — | — | — | 12.517 | 6.5 | 12.517 |
| 48 h (mg/well) | PEI without Dox | — | — | — | — | — | — | — |
| | Dox | | — | 0.0688 | 0.0271 | 0.036 | 0.016 | 0.034 |
| | PEI | | | 2.966 | 1.168 | 1.552 | 0.690 | 1.466 |
| PEI/Dox with PEI-25k | | No Dox / No PEI | 0.1 | 0.2 | 0.4 | 0.6 | 0.67 | 1 |
| 24 h (µM) | Dox | — / — | 3.123 | 2.102 | 1.987 | 0.608 | 0.506 | 0.274 |
| | PEI | | 0.312 | 0.420 | 0.795 | 0.365 | 0.337 | 0.274 |
| 48 h (µM) | Dox | — / — | 1.651 | 1.108 | 1.054 | 0.374 | 0.291 | 0.204 |
| | PEI | | 0.165 | 0.222 | 0.422 | 0.224 | 0.194 | 0.204 |

— means not able be detected

Figure 3:
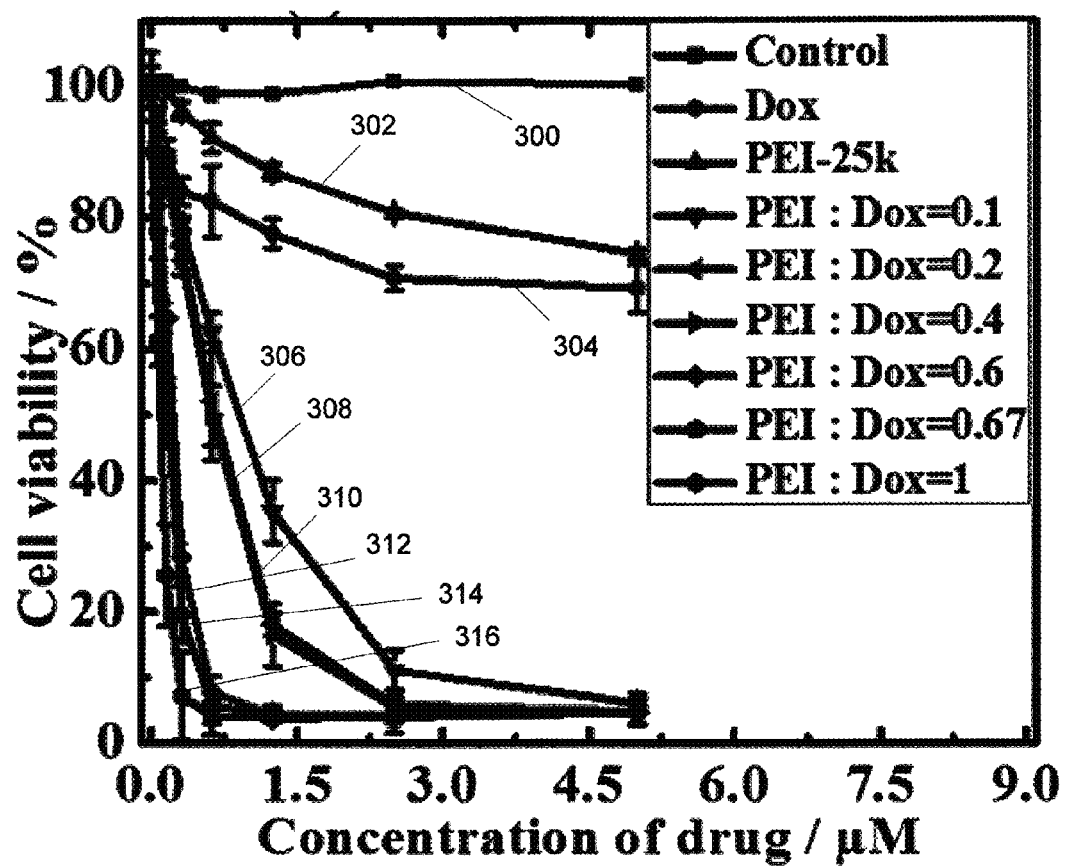
FIG. 3 is a graph depicting cell viability as a function of drug concentration for various compositions that alter the ratio of polymer to chemotherapeutic drug.

FIG. 3 depicts the results of changing the ratio of cationic polymer to doxorubicin. Line 300 depicts a control where a MDA MB 231 cell line was permitted to grow for 24 hours. Line 302 shows cell viability (about 80%) in the presence of PEI-25k at a PEI:doxorubicin ratio of 1:0.2. The additional of PEI amplified the toxicity five-fold. The x-axis is 2.5 µM and the PEI concentration is 0.5 µM. Line 304 shows cell viability (about 70%) in the presence of various concentrations of doxorubicin (less than 5 µM). Line 306 shows the effects of a 1:0.1 molar ratio of PEI:doxorubicin that reduced cell viability to 35-40% at a doxorubicin concentration of 1.5 µM which drops to less than 10% at higher concentrations. Line 308 and line 310 show the effects of compositions with a PEI:doxorubicin molar ratio of 1:0.2 and 1:0.4, respectively. Both line 308 and line 310 had similar profiles with cell viabilities of 15-20% at a doxorubicin concentration of 1.5 µM which drops to less than 10% at higher concentrations. Lines 312, 314 and 316 show the effects of compositions with a PEI:doxorubicin of 1:0.6; 1:0.67 and 1:1, respectively. All three lines had similar profiles with cell viabilities of less than 5% at a doxorubicin concentration of 1.5 µM. In one embodiment a ratio of at least 1:0.5 (PEI: doxorubicin, i.e. at least a 2:1 ratio) is used and such an embodiment permits the use of a low concentration of doxorubicin and still provides an excellent reduction in cell viability. In one embodiment, the composition has a co-drug to drug ratio of between 0.1:1 and 10:1. In another embodiment, the ratio is between 1:1 and 5:1. In another embodiment the ratio is between 2:1 and 5:1.

Figure 4:
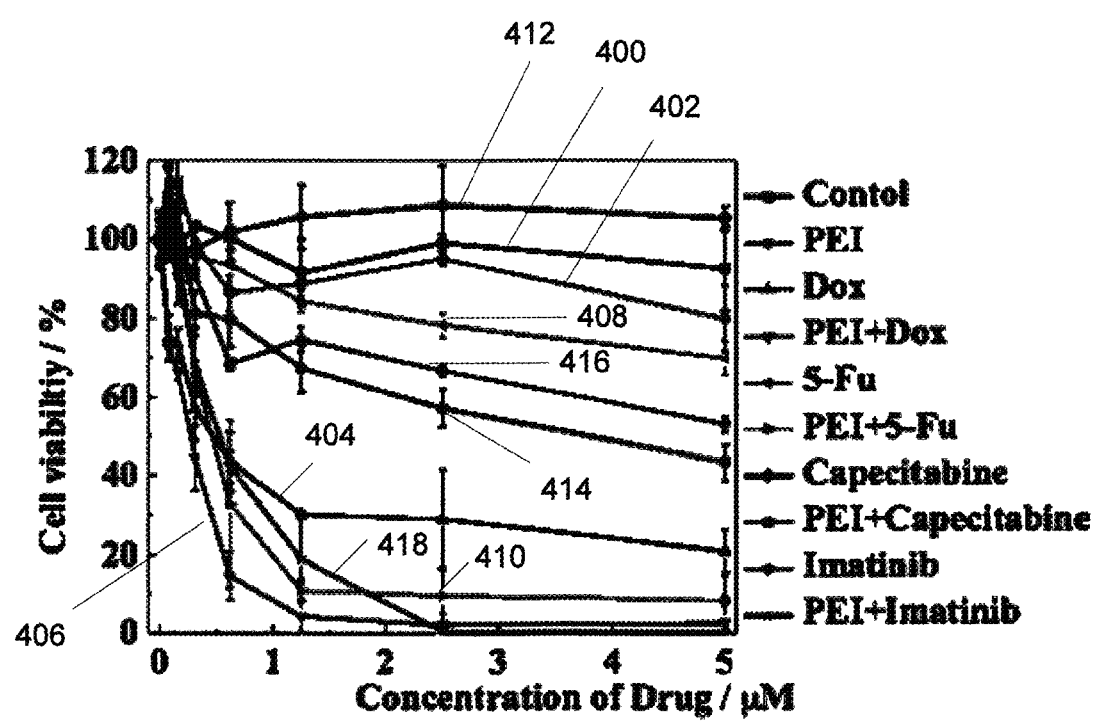
FIG. 4 depicts co-administration of PEI and other cationic drug to Hs 587T cells.

FIG. 4 depicts co-administration of PEI and other cationic drug to Hs 587T cells (here PEI concentration has amplified five times for uniform display. Line 400 is a control. Line 402 shows PEI. Line 404 shows doxorubicin. Line 406 shows the combined PEI and doxorubicin. Line 408 shows fluorouracil (5-FU). Line 410 shows the combined PEI and 5-FU. Line 412 shows capecitabine. Line 414 shows the combined PEI and capecitabine. Line 416 shows imatinib. Line 418 shows the combined PEI and imatinib.

Figure 5:
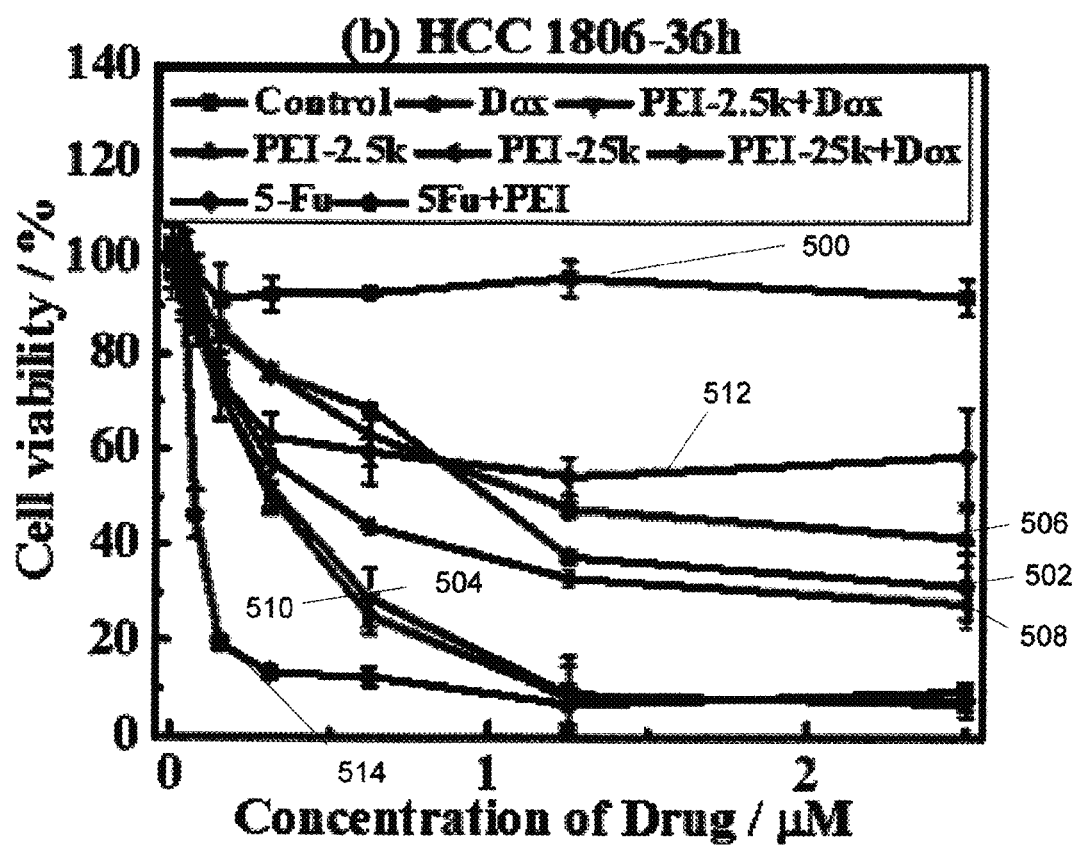
FIG. 5 depicts the co-administration of PEI and other cationic drugs to HCC 1806 cells.

FIG. 5 depicts the co-administration of PEI and other cationic drugs to HCC 1806 cells (here PEI concentration has amplified five times for uniform display). Line 500 is a control. Line 502 shows doxorubicin. Line 504 shows the combined PEI-2.5k and doxorubicin. Line 506 shows PEI-2.5k. Line 508 shows PEI-25k. Line 510 shows the combined PEI-25k and doxorubicin. Line 512 shows 5-FU. Line 514 shows the combined 5-FU and PEI.

Figure 6:
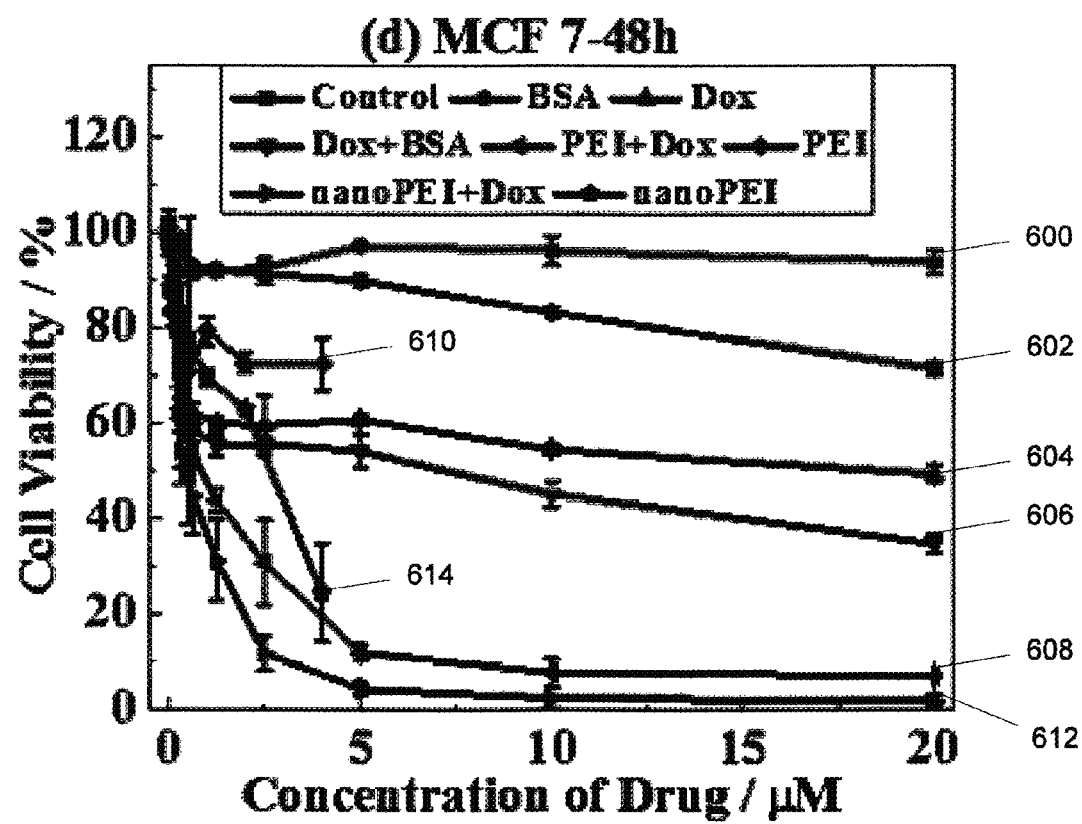
FIG. 6 depicts the co-administration of PEI and nanoPEI and other cationic drugs to MCF 7 cells.

FIG. 6 depicts the co-administration of PEI and nanoPEI and other cationic drugs to MCF 7 cells. Line 600 is a control. Line 602 shows BSA. Line 604 shows doxorubicin. Line 606 shows the combined BSA and doxorubicin. Line 608 shows the combined PEI and doxorubicin. Line 610 shows PEI. Line 612 shows the combined nanoPEI and doxorubicin. Line 614 shows nanoPEI.

Figure 7:
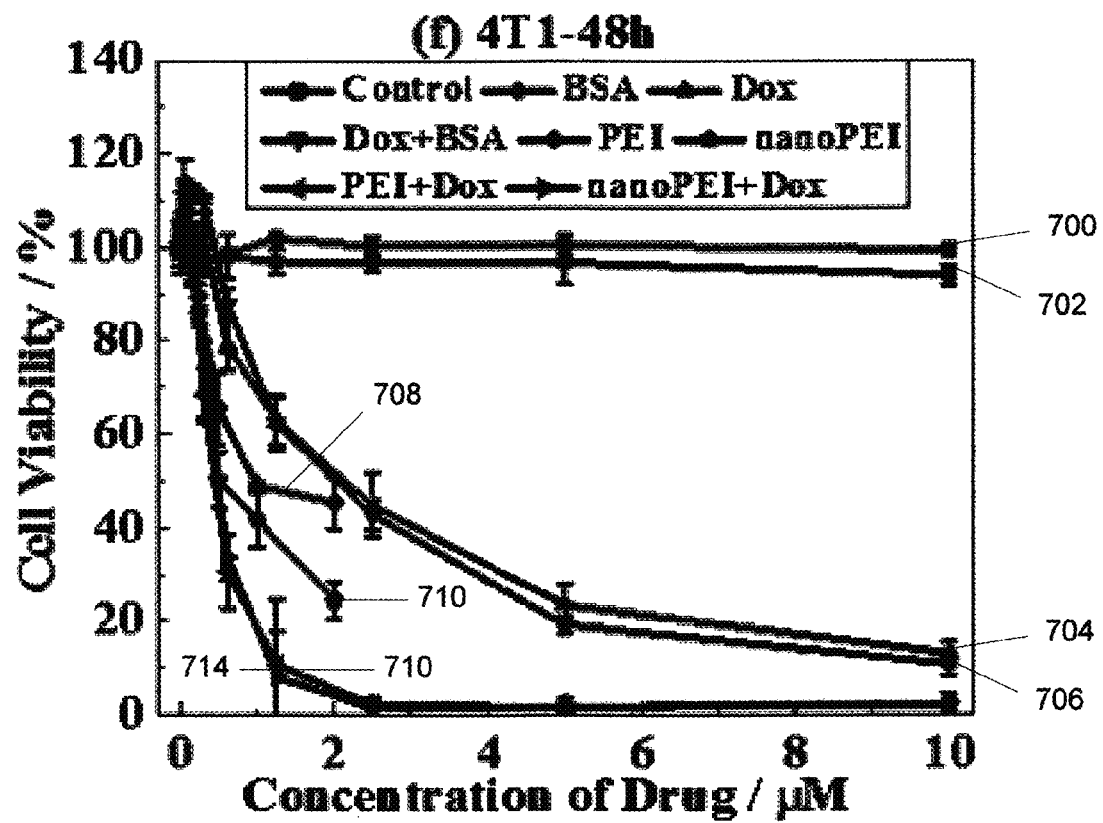
FIG. 7 depicts the co-administration of PEI and nanoPEI and other cationic drugs to 4T1 cells.

FIG. 7 depicts the co-administration of PEI and nanoPEI and other cationic drugs to 4T1 cells. Line 700 shows a control. Line 702 shows BSA. Line 704 shows doxorubicin. Line 706 shows the combined BSA and doxorubicin. Line 708 sows PEI. Line 710 shows nanoPEI. Line 712 shows the combined PEI and doxorubicin. Line 714 shows the combined nanoPEI and doxorubicin.

Figure 8:
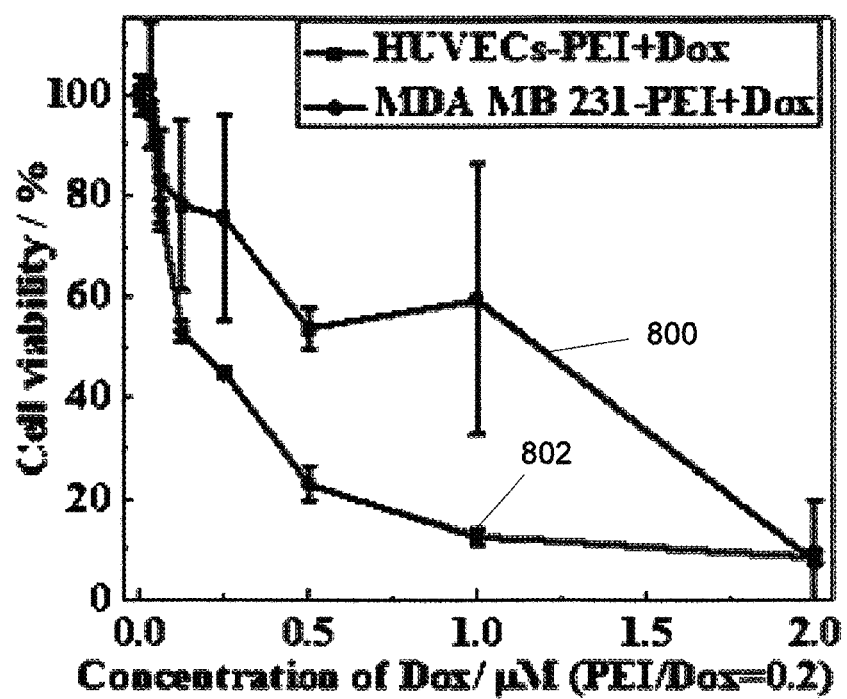
FIG. 8 depicts the co-administration of PEI and doxorubicin on normal cells (HUVECs) and cancer cells (MDA MB 231)

FIG. 8 depicts the co-administration of PEI and doxorubicin on normal cells (HUVECs, line 800) and cancer cells (MDA MB 231, line 802).

Figure 9A:
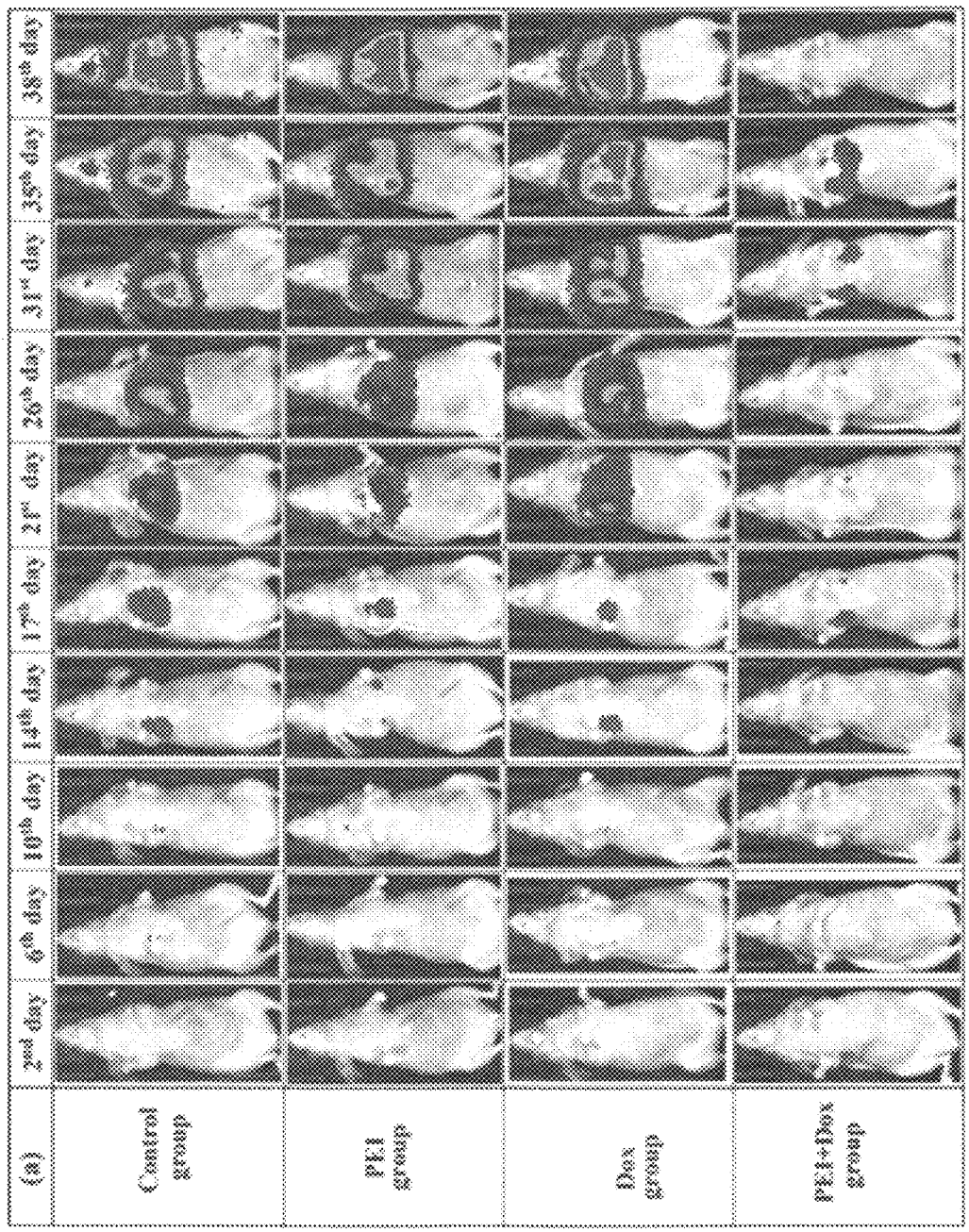
FIG. 9A show a visible comparison of the tumor signal developing trend of a control group, a doxorubicin group, a PEI group, and a combined PEI plus doxorubicin group.
Figure 9B:
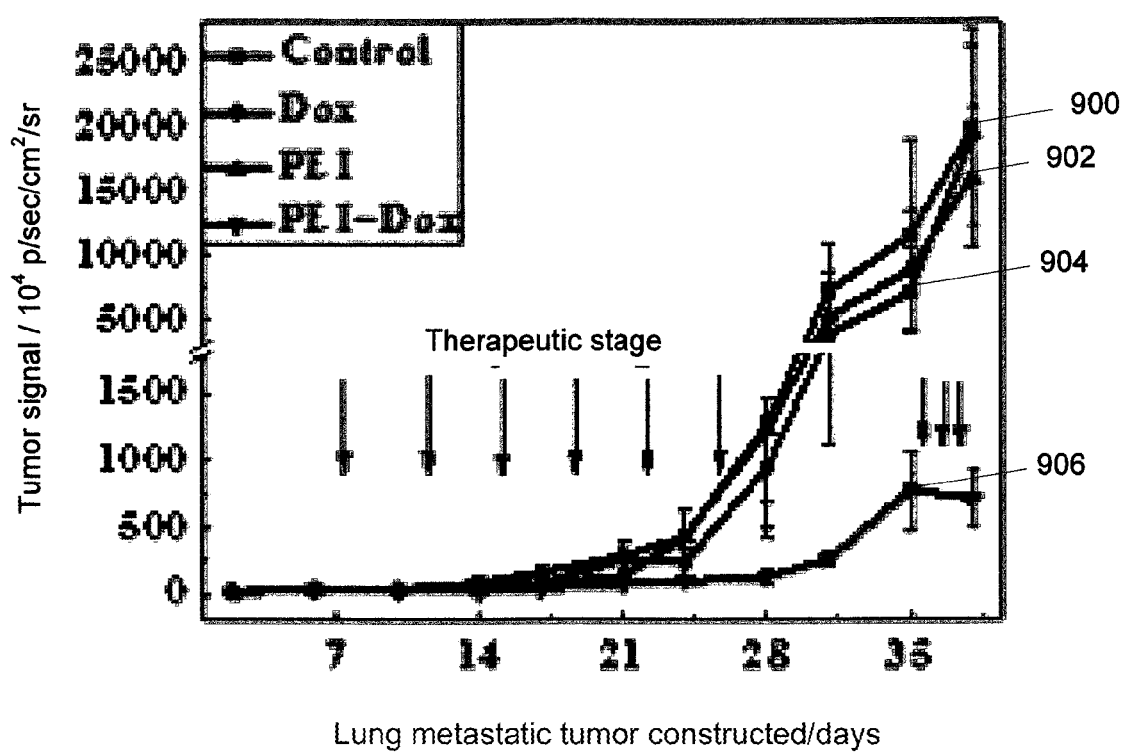
FIG. 9B shows the tumor signal trend of the control group, the doxorubicin group, the PEI group, and the combined PEI plus doxorubicin group.
Figure 9C:
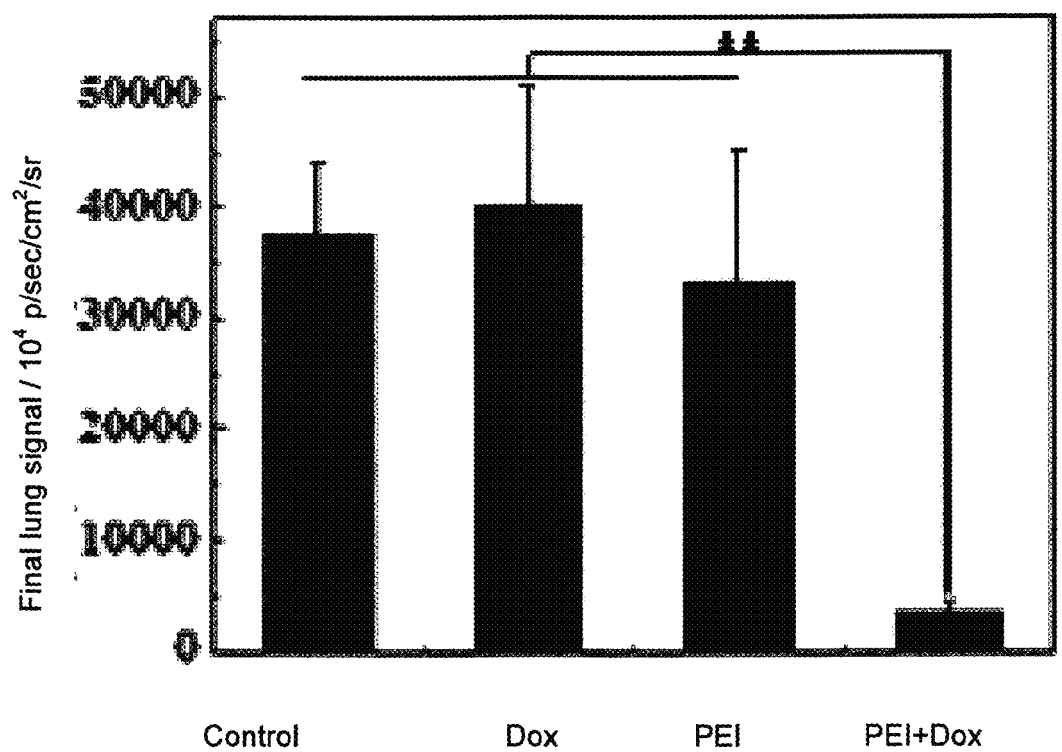
FIG. 9C shows the final tumor signal of the control group, the doxorubicin group, the PEI group, and the combined PEI plus doxorubicin group.
Figure 9D:
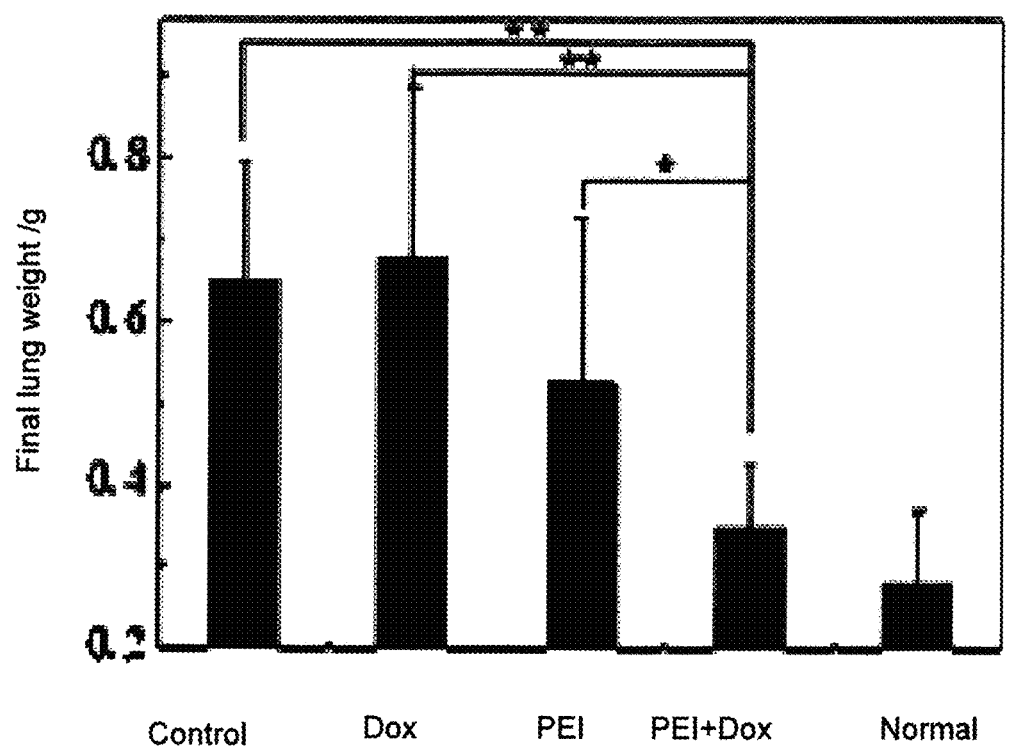
FIG. 9D shows final lung weight of the control group, the doxorubicin group, the PEI group, and the combined PEI plus doxorubicin group.

FIG. 9A show a visible comparison of the tumor signal developing trend of a control group, a doxorubicin group, a PEI group, and a combined PEI plus doxorubicin group. FIG. 9B shows the tumor signal trend of the control group 900, the doxorubicin group 902, the PEI group 904, and the combined PEI plus doxorubicin group 906. FIG. 9C shows the final tumor signal of the control group, the doxorubicin group, the PEI group, and the combined PEI plus doxorubicin group. FIG. 9D shows final lung weight of the control group, the doxorubicin group, the PEI group, and the combined PEI plus doxorubicin group.

Figure 10A:
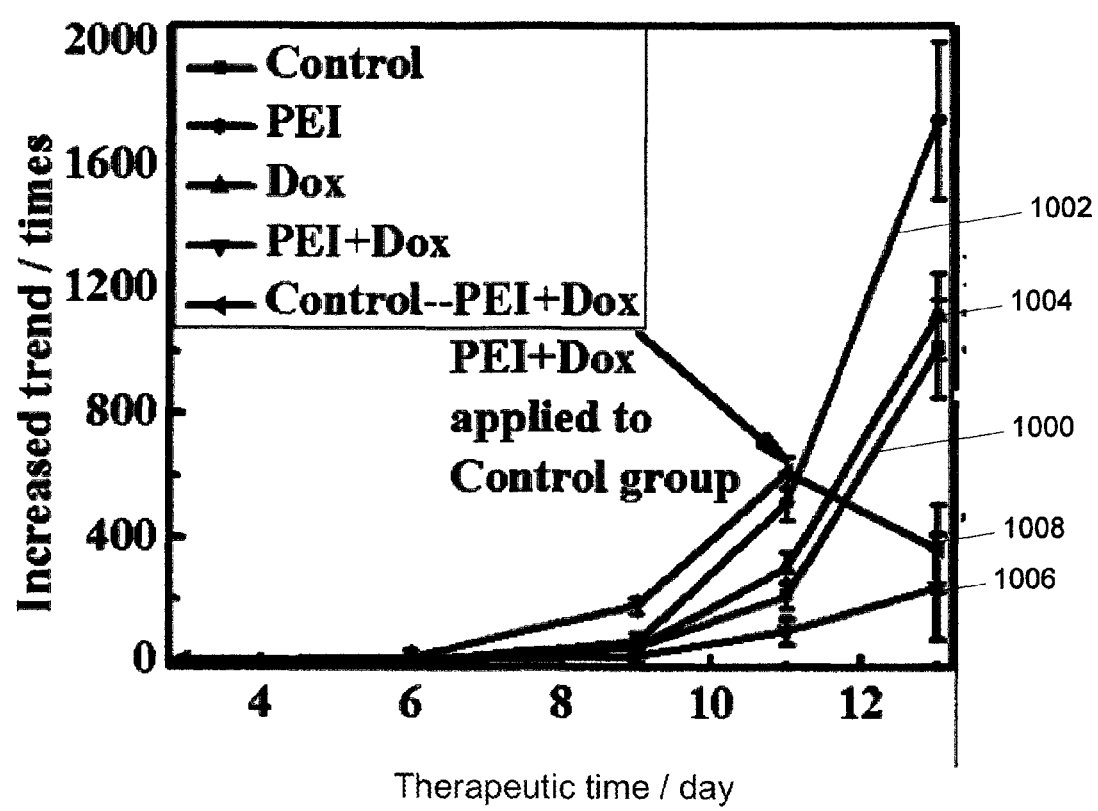
FIG. 10A shows the therapeutic effect determined by the increased trend of a control group, a doxorubicin group, a PEI group, a combined PEI plus doxorubicin group and a combined PEI plus doxorubicin reverse group.
Figure 10B:
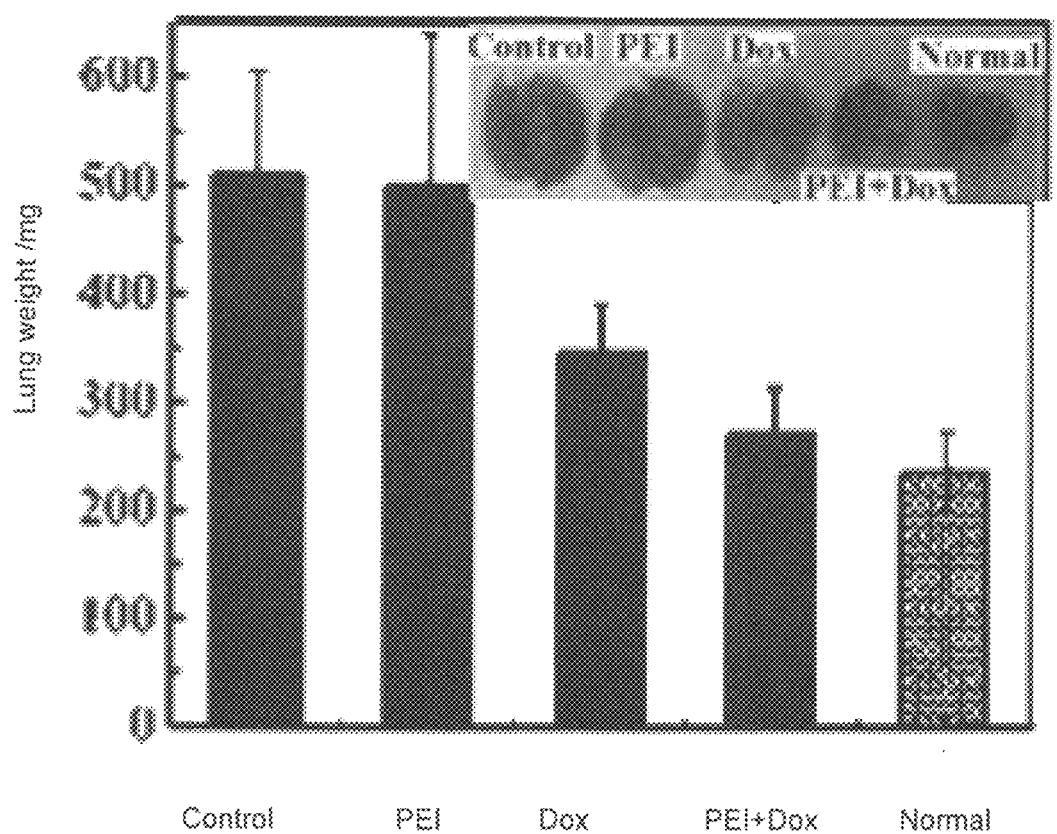
FIG. 10B shows final lung weight and size among the control group, the doxorubicin group, the PEI group, the combined PEI plus doxorubicin group and a normal group.

FIGS. 10A to 10D shows in vivo synergistic chemotherapy through ectopic models of lung metastasis (4T1 breast cancer metastasis model on BabL/c mice). FIG. 10A shows the therapeutic effect determined by the increased trend of a control group 1000, a doxorubicin group 1004, a PEI group 1002, a combined PEI plus doxorubicin group 1006 and a combined PEI plus doxorubicin reverse group 1008. FIG. 10B shows final lung weight and size among the control group, the doxorubicin group, the PEI group, the combined PEI plus doxorubicin group and a normal group.

Figure 10C:
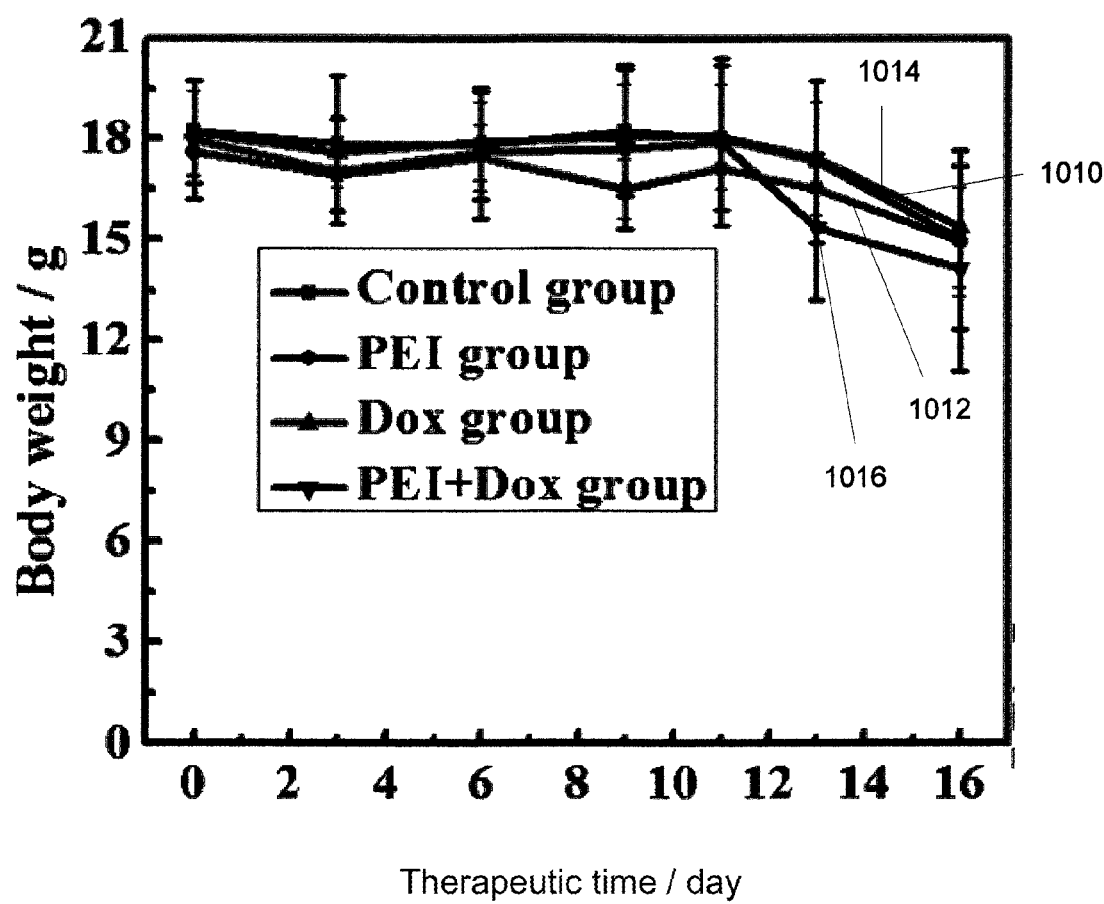
FIG. 10C shows body weight of the different groups.
Figure 10D:
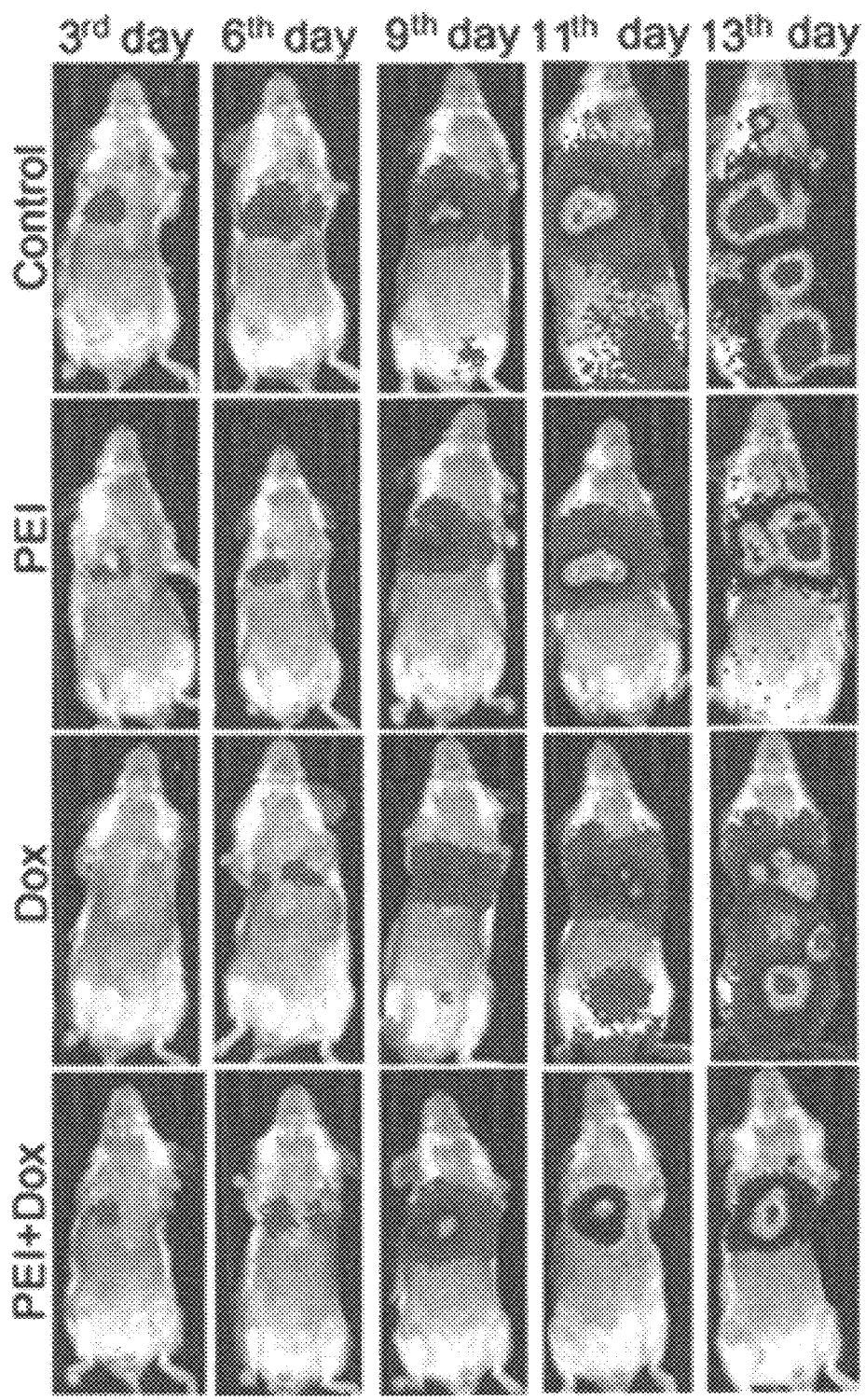
FIG. 10D shows a comparison of the tumor metastatic signal among the control group, the doxorubicin group, the PEI group, the combined PEI pus doxorubicin group.

FIG. 10C shows body weight of the different groups. FIG. 10D shows a comparison of the tumor metastatic signal among the control group, the doxorubicin group, the PEI group, the combined PEI pus doxorubicin group. In FIG. 10D, the drug was administrated after seven days of tumor model construction for the control group, the doxorubicin group, the PEI group, the combined PEI plus doxorubicin group, and ten days for the combined PEI plus doxorubicin reversed group.

The proportions of cationic polymer and drug can also change dependent on the identity of the two components and administration style. For example, PEI mixed with doxorubicin has two desirable concentrations: (1) 0.01 to 10 μg PEI for every 1 μg Dox when administrated subsequently and (2) 10 to 100 μg PEI for every 1 μg Dox when administered together.

In one embodiment, the method simply mixes a cationic polymers and a cytotoxic drug. No covalent linking or functionalized with nuclear localizing signals (NLSs) is performed. One advantage of the method is the simplicity of mixing the cationic polymers and the chemotherapeutic drug together to achieve the desirable therapeutic effect on cancer therapy. The two components have a synergistic function to execute the therapeutic program.

A simple cationic polymer can efficiently enter cells and localize in the nuclei itself or help other molecules (such as DNA or RNA) enter into the nuclei. Without wishing to be bound to any particular theory, the mechanism of drug delivery into the nucleus is believed to be an electrostatic interaction between the cationic polymer and anionic lipids, DNA or RNA. The cationic polymer can increase the delivery of cytotoxic drug (e.g., doxorubicin, fluorouracil (5-FU)) to enhance the drug effectiveness. The cationic polymer and drug have a synergistic effect.

The administration style is flexible. The administration can be executed by mixing the cationic polymer and drug together at the specific site of treatment or by the local release of cationic polymer and systemic delivery of drug separately, but simultaneously. The administration can be carried out by the sequential administration of the two components. The components can be injected into the intraperitoneal cavity, intravenous, or intratumoral.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for treating a biological cell, the method comprising:
    administering a composition of matter to a biological sample, wherein the composition of matter comprises a mixture of:
    a chemotherapeutic drug and a branched polylysine wherein the chemotherapeutic drug is not covalently bound to the branched polylysine;
    wherein the composition of matter exhibits greater cytotoxicity than either the chemotherapeutic drug or the branched polylysine individually.

2. A method for treating a biological cell, the method comprising:
    administering a composition of matter to a biological sample, wherein the composition of matter comprises a mixture of:
    a chemotherapeutic drug and an $\epsilon$-polylysine (EPL) wherein the chemotherapeutic drug is not covalently bound to the $\epsilon$-polylysine (EPL);
    wherein the composition of matter exhibits greater cytotoxicity than either the chemotherapeutic drug or the $\epsilon$-polylysine (EPL) individually.

3. The method as recited in claim 1, wherein the composition of matter has a molar ratio of between 0.1:1 and 10:1 (moles of the branched polylysine:moles of the chemotherapeutic drug).

4. The method as recited in claim 1, wherein the composition of matter has a molar ratio of between 1:1 and 5:1 (moles of the branched polylysine:moles of the chemotherapeutic drug).

5. The method as recited in claim 1, wherein the composition of matter has a molar ratio of between 2:1 and 5:1 (moles of the branched polylysine:moles of the chemotherapeutic drug).

6. The method as recited in claim 2, wherein the composition of matter has a molar ratio of between 0.1:1 and 10:1 (moles of the $\epsilon$-polylysine (EPL):moles of the chemotherapeutic drug).

7. The method as recited in claim 2, wherein the composition of matter has a molar ratio of between 1:1 and 5:1 (moles of the $\epsilon$-polylysine (EPL):moles of the chemotherapeutic drug).

8. The method as recited in claim 2, wherein the composition of matter has a molar ratio of between 2:1 and 5:1 (moles of the $\epsilon$-polylysine (EPL):moles of the chemotherapeutic drug).

9. A composition of matter comprising a mixture of:
    a chemotherapeutic drug and a branched polylysine;
    wherein the chemotherapeutic drug is not covalently bound to the branched polylysine; and
    wherein the composition of matter exhibits greater cytotoxicity than either the chemotherapeutic drug or the branched polylysine individually.

10. A composition of matter comprising a mixture of:
    a chemotherapeutic drug and an $\epsilon$-polylysine (EPL);
    wherein the chemotherapeutic drug is not covalently bound to the $\epsilon$-polylysine (EPL); and
    wherein the composition of matter exhibits greater cytotoxicity than either the chemotherapeutic drug or the $\epsilon$-polylysine (EPL) individually.

* * * * *